US012226078B2

United States Patent
Still et al.

(10) Patent No.: US 12,226,078 B2
(45) Date of Patent: Feb. 18, 2025

(54) EUS VALVE ASSEMBLIES

(71) Applicant: UNITED STATES ENDOSCOPY GROUP, INC., Mentor, OH (US)

(72) Inventors: Rapheal Still, Richmond Heights, OH (US); Gary E. Mann, Painesville, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 766 days.

(21) Appl. No.: 16/951,343

(22) Filed: Nov. 18, 2020

(65) Prior Publication Data

US 2021/0145261 A1  May 20, 2021

Related U.S. Application Data

(60) Provisional application No. 62/936,921, filed on Nov. 18, 2019.

(51) Int. Cl.
  *A61B 1/015* (2006.01)
  *A61B 1/00* (2006.01)
(52) U.S. Cl.
  CPC .......... *A61B 1/015* (2013.01); *A61B 1/00068* (2013.01); *A61B 1/00094* (2013.01); *A61B 1/00137* (2013.01)
(58) Field of Classification Search
  CPC .............................. A61B 1/00068; A61B 1/015
  See application file for complete search history.

(56) References Cited

U.S. PATENT DOCUMENTS

| | | | |
|---|---|---|---|
| 4,261,343 A | | 4/1981 | Ouchi et al. |
| 4,537,209 A | * | 8/1985 | Sasa ................. A61B 1/125 134/102.1 |
| 4,779,624 A | | 10/1988 | Yokoi |
| 4,794,913 A | * | 1/1989 | Shimonaka ......... A61M 1/7413 600/154 |

(Continued)

FOREIGN PATENT DOCUMENTS

| | | |
|---|---|---|
| JP | 56 143132 A | 11/1981 |
| JP | 2005261512 A | 9/2005 |

(Continued)

OTHER PUBLICATIONS

Inviation to Pay Additional Fees from PCT/US20/60996 dated Feb. 8, 2021.

(Continued)

*Primary Examiner* — John P Leubecker
(74) *Attorney, Agent, or Firm* — Calfee, Halter & Griswold LLP

(57) ABSTRACT

A disposable air and water (AW) valve assembly and suction valve assembly for an EUS instrument. The AW assembly includes an AW valve and an endcap for receiving the AW valve therebetween. The AW valve includes an AW stem connected to a valve stem. The suction valve assembly includes a suction valve disposed in a suction endcap. The suction valve also includes a valve stem. The valve stem is disposed between a suction valve opening such that portions of the valve stem extend beyond opposed ends of the suction endcap. The suction valve is formed from a suction stem and a piston connected to the suction stem.

15 Claims, 13 Drawing Sheets

(56) References Cited

U.S. PATENT DOCUMENTS

| | | | |
|---|---|---|---|
| 4,800,869 A * | 1/1989 | Nakajima | A61B 1/00068 600/158 |
| 4,860,731 A * | 8/1989 | Matsuura | A61B 1/00068 600/110 |
| 4,979,497 A * | 12/1990 | Matsuura | A61B 1/042 600/921 |
| 5,027,791 A | 7/1991 | Takahashi | |
| 5,840,016 A * | 11/1998 | Kitano | A61B 1/12 251/335.2 |
| 5,871,441 A | 2/1999 | Ishiguro et al. | |
| 6,346,075 B1 | 2/2002 | Arai et al. | |
| 8,460,179 B2 | 6/2013 | Ikeda et al. | |
| 11,369,256 B2 | 6/2022 | Saiga et al. | |
| 2012/0071843 A1 | 3/2012 | Yamane | |
| 2012/0088973 A1 | 4/2012 | Morimoto | |
| 2013/0303844 A1 * | 11/2013 | Grudo | A61B 1/00064 600/101 |
| 2019/0125167 A1 * | 5/2019 | Taniguchi | A61B 1/015 |
| 2020/0375434 A1 * | 12/2020 | Scutti | A61B 1/00137 |

FOREIGN PATENT DOCUMENTS

| | | |
|---|---|---|
| JP | 2007014439 A | 1/2007 |
| JP | 2007111255 A | 5/2007 |
| JP | 2007111266 A | 5/2007 |
| WO | 2018136274 A1 | 7/2018 |

OTHER PUBLICATIONS

International Search Report and Written Opinion from PCT/US20/60996 dated May 17, 2021 (17 pages).

Pentax® OF-B171 Literature, Suction Control Valve Model OF-B171 (including O-Ring Set OF-B187) for PENTAX Ultrasound GI Videoscopes: Model EG-3870UTK/EG-3670URK, Jul. 2008, 1 page.

Pentax® OF-B172 Literature, Air/Water/Balloon Feeding Valve Model OF-B172 (Including O-Ring Set OF-B191) for PENTAX Ultrasound GI Videoscopes: Model EG-3870UTK/EG-3670URK, Jul. 2008, 1 page.

* cited by examiner

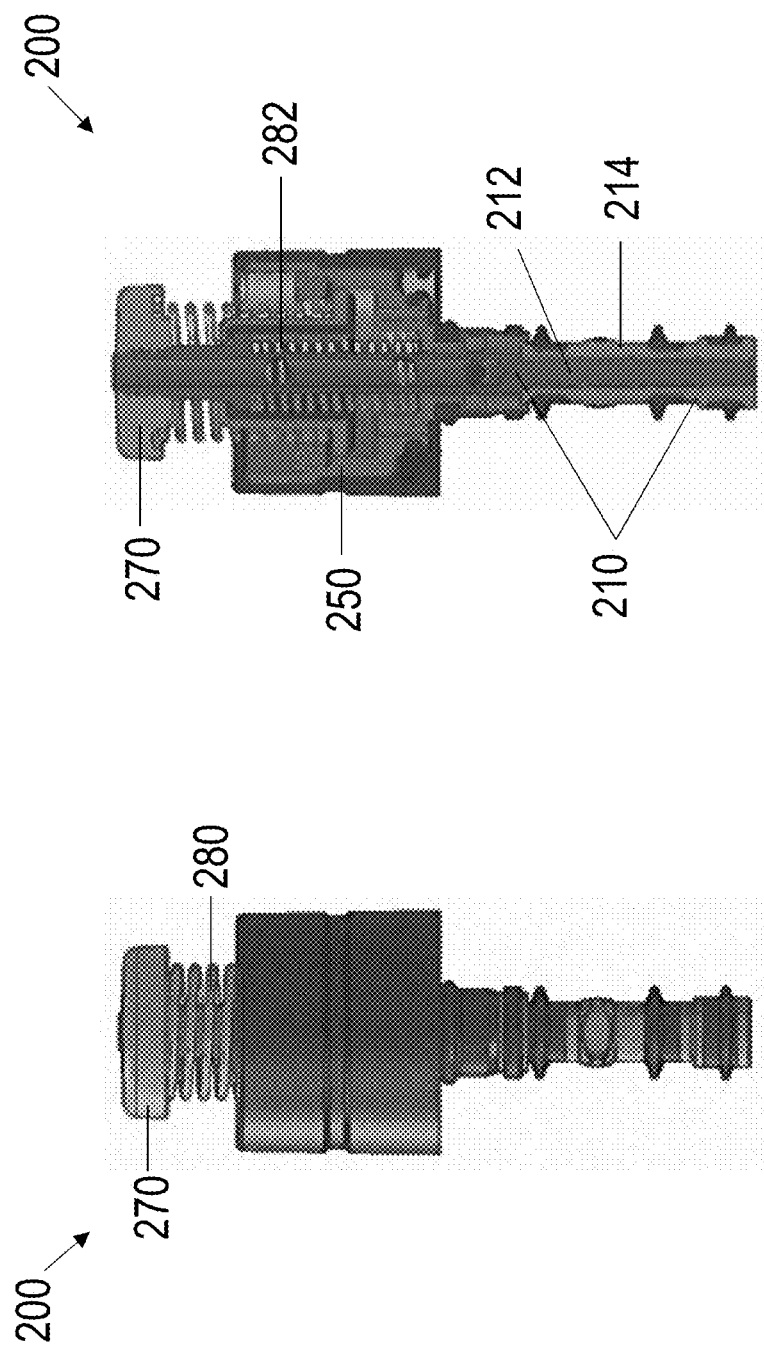

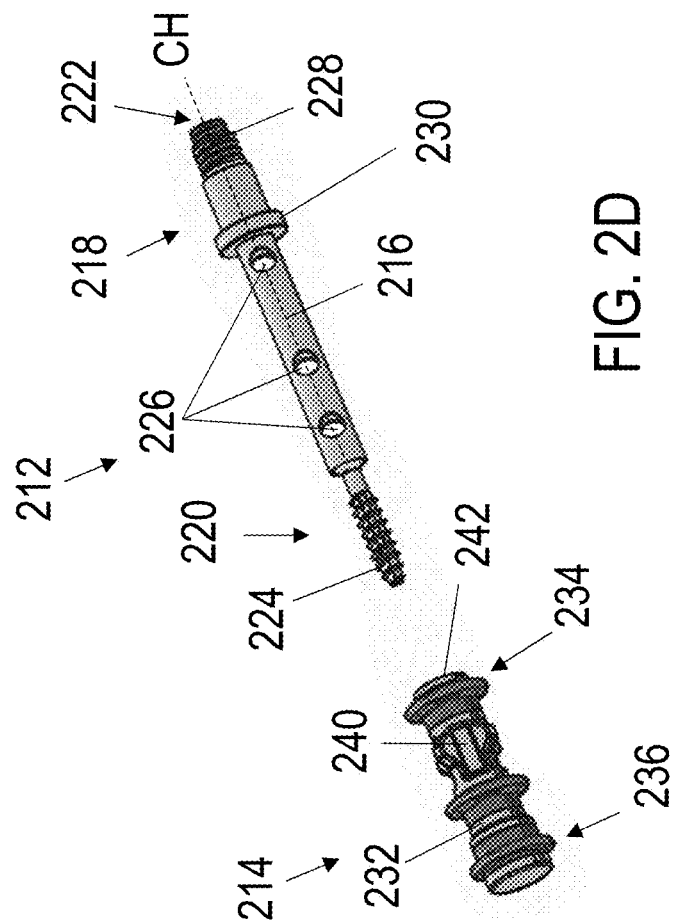

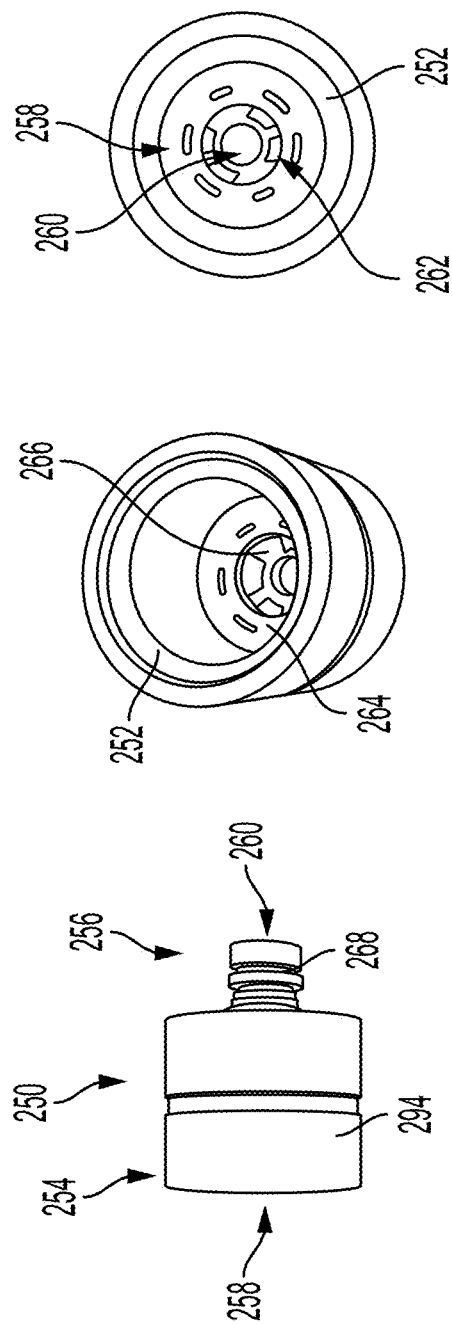

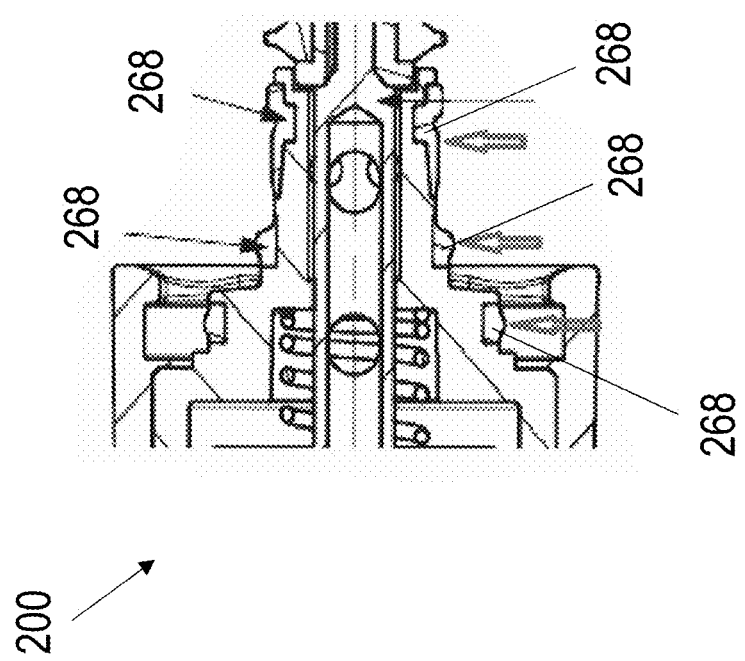

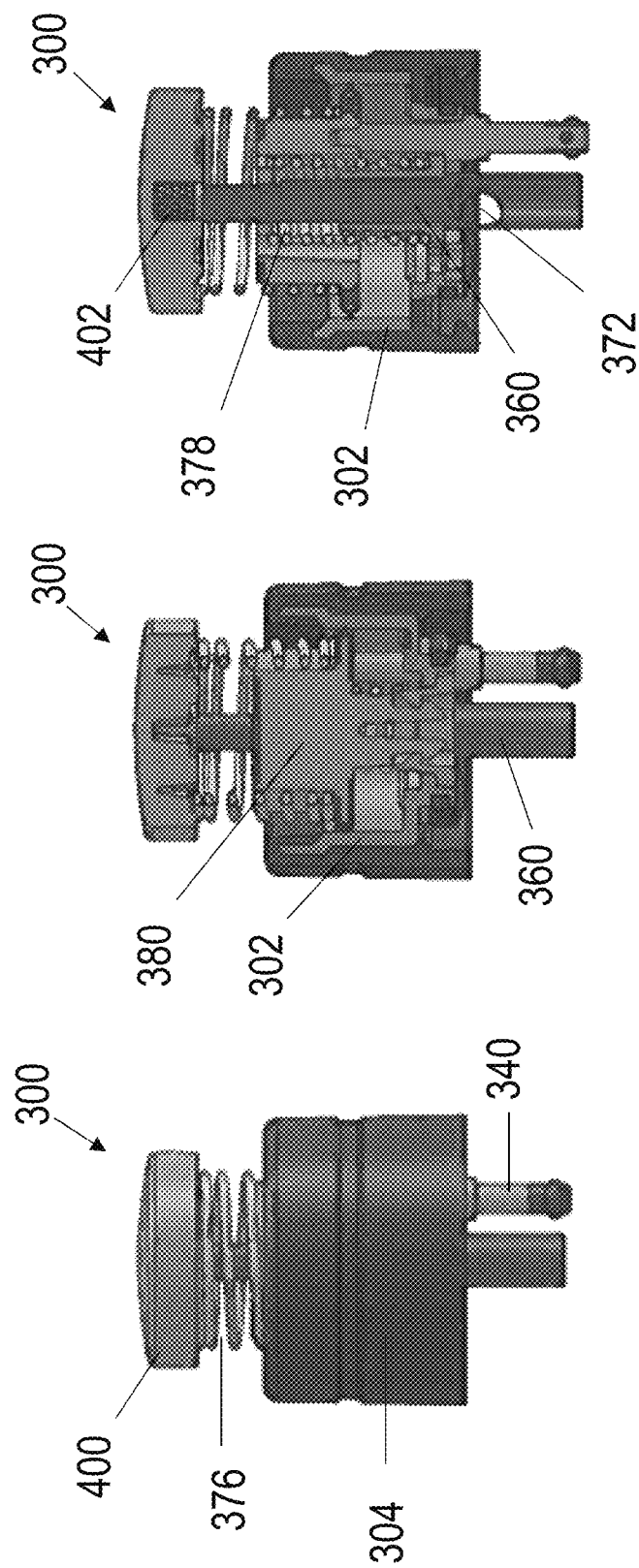

EUS VALVE ASSEMBLIES

CROSS-REFERENCE TO RELATED APPLICATIONS

The present application claims benefits and priority to U.S. Provisional Patent Application No. 62/936,921, filed on Nov. 18, 2019, the entire disclosure of which is incorporated herein by reference.

TECHNICAL FIELD

The present disclosure relates generally to endoscopic ultrasounds (EUS) and, more specifically, to valve assemblies for use with EUS instruments during EUS procedures.

BACKGROUND

EUS air/water (AW) valves and EUS suction valves are used for controlling an air/water function and suction function on an Endoscope, e.g., and Echo Endoscope as well as the inflation and deflation of an EUS balloon during an endoscopic procedure (e.g., a gastrointestinal (GI) tract procedure). Traditional AW and suction valves (collectively referred to as the "traditional valves") are reprocessable (i.e., reusable medical equipment) given their construction and the costs associated with their manufacturing, assembling, use, and reuse (collectively referred to as "use costs").

Although the purchase cost for the traditional valves may be a fixed one-time cost, the reuse costs for the traditional valves vary and are difficult to predict. This difficulty may be based on the nature of the GI procedure, which involves exposing valves to contaminants which may result from the GI procedure, and the construction of the traditional valves, which involves many difficult to reach components without disassembly, and an inability to clean and sterilize each of the traditional valves after a first pass through a cleaning and sterilizing process (the "cleaning" process). Multiple passes through this cleaning process may be necessary before the traditional valves can be reused, with each pass through the cleaning process adding to the use costs for each traditional valve.

Potential delays for having the traditional valves available for reuse may result due to multiple passes through the cleaning process, which may lead operators and users of the endoscope to purchase multiple traditional valves, which also have to go through the cleaning process after each use, thereby adding to their use costs, and the overall costs associated with using the endoscope. The increased overall costs may lead to increased medical costs for operators who rely on endoscopes, which may also lead to increased patient costs for much needed procedures involving endoscopes.

SUMMARY

Due to the difficulties with predicting the availability of reused/reprocessed traditional valves, and due to the increased overall costs associated with owning and reusing the traditional valves, a need exists for disposable EUS valve assemblies to eliminate the unavailability issues and reuse costs associated with the traditional valves, and also to remove the possibility of patient or operator contamination and/or infection resulting from traditional valves unsuccessfully reprocessed.

In one exemplary embodiment, an endoscopy valve assembly (e.g., an endoscopic ultrasound air and water valve assembly) is provided. The assembly includes at least an air and water (AW) valve, and an endcap configured to receive at least a portion of the AW valve therebetween. The AW valve includes at least a valve stem and an AW stem at least partially disposed within a valve stem opening of the valve stem. The AW stem and the valve stem are each formed of a single piece construction.

In yet another exemplary embodiment, an endoscopy valve assembly (e.g., an endoscopic ultrasound suction valve assembly) is provided. The assembly includes at least an endcap having a first endcap opening and a suction valve at least partially disposed between the first endcap opening. The suction valve includes a suction valve opening and a valve stem at least partially disposed between the suction valve opening. The valve stem is disposed such that portions of the valve stem extend beyond opposed ends of the endcap. The suction valve includes a suction stem having an elongated suction stem part that extends from a first side of the suction stem beyond one end of the endcap. The assembly further includes a piston connected to a second side of the suction stem opposite the first side. The suction stem and the piston are each formed of a single piece construction.

These and other objects, features and advantages of the present disclosure will become apparent from the following detailed description of illustrative embodiments thereof, which is to be read in connection with the accompanying drawings.

BRIEF DESCRIPTION OF THE DRAWINGS

These and other features of the present disclosure will become better understood with regard to the following description and accompanying drawings in which:

FIG. 2A illustrates an exemplary embodiment of an air and water valve assembly in accordance with the disclosure provided herein;

FIG. 2B illustrates a sectional view of the air and water valve assembly of FIG. 2A;

FIG. 2C illustrates an exemplary embodiment of an air and water valve in accordance with the disclosure provided herein;

FIG. 2D illustrates an exploded view of the air and water valve of FIG. 2C;

FIG. 2G illustrates an exemplary embodiment of an endcap in accordance with the disclosure provided herein;

FIG. 2H illustrates an enlarged cross-sectional view of a portion of an exemplary embodiment of an air and water valve assembly in accordance with the disclosure provided herein;

FIG. 3A illustrates an exemplary embodiment of a suction valve (SV) assembly in accordance with the disclosure provided herein;

FIG. 3B illustrates a sectional view of an embodiment of the suction valve assembly of FIG. 3A;

FIG. 3C illustrates a second sectional view of an embodiment of the suction valve assembly of FIG. 3A;

DETAILED DESCRIPTION

Aspects and implementations of the present disclosure will be understood more fully from the detailed description given below and from the accompanying drawings of the various aspects and implementations of the disclosure. This should not be taken to limit the disclosure to the specific aspects or implementations, but explanation and understanding only.

Figure 1:
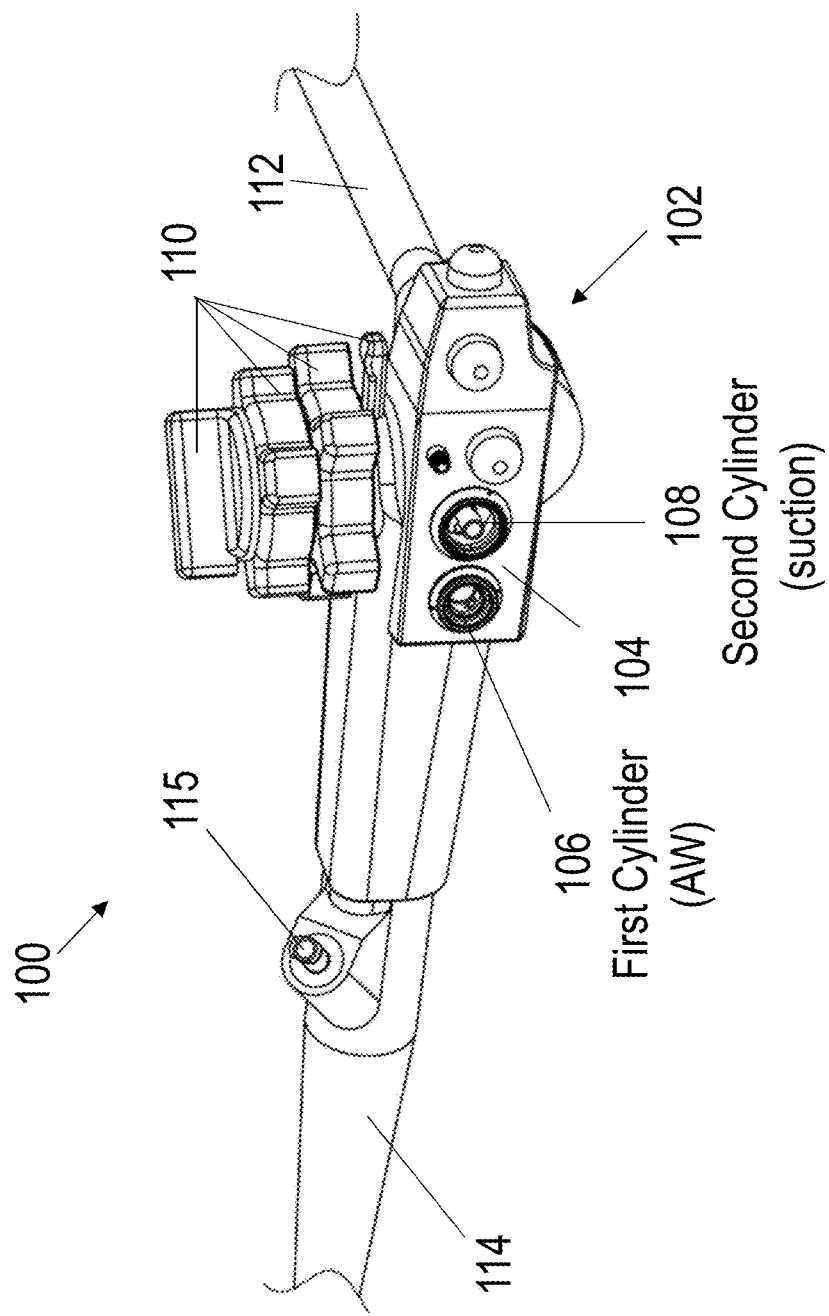
FIG. 1 illustrates an exemplary embodiment of an endoscope instrument, in accordance with the disclosure provided herein.

Referring now to the drawings, which are for purposes of illustrating exemplary embodiments of the subject matter herein only, and not for limiting the same, FIG. 1 shows an exemplary embodiment of an endoscopy ultrasound (EUS) instrument 100 (e.g., an Echo endoscopy instrument). In discussing the exemplary embodiments herein, the terms "proximal" and "distal" may often be used. These terms are used to describe a position or a direction with reference to the operator of the instrument. For example, the proximal position or proximal direction is toward the user or operator of the instrument, and the distal position or direction is away from the user or operator of the instrument, i.e., position or direction toward the object which the operator is attempting to grasp, retain, and/or view.

As shown in FIG. 1, the EUS instrument 100 may include at least a handheld portion 102 which may be held by an operator or similar user of the EUS instrument 100 during an EUS procedure. The handheld portion 102 may include at least a casing or similar housing 104. The casing 104 may include one or more cylinders or similar openings for housing or at least partially encompassing one or more assemblies (e.g., one or more valve assemblies) and/or similar control systems therein. As shown in FIG. 1, the casing 104 may include at least a first cylinder 106 and a second cylinder 108 for at least partially receiving a first and second valve assembly therein. Additionally, or alternatively, the casing 104 may include one or more controllers 110 (at least four shown in FIG. 1) operably connected thereto, for interfacing or otherwise controlling one or more devices or EUS systems. Examples of the controlled functions may include a left and right motion, an up and down motion, and a locking of the left and right or up and down motions.

The EUS systems may include, for example, a suction system, a supply system (e.g., an air supply system and/or a water supply system), or any other system known in the art to be used with the EUS instrument 100 and/or during an EUS procedure. It should be appreciated that the EUS instrument 100 may be connected to one or more of the EUS systems via one or more umbilical tubes 112 (FIG. 1).

In some embodiments, the EUS instrument 100 may further include an EUS instrument hose 114 having one or more tubes extending distally from the EUS instrument 100 and an instrument channel 115. In some embodiments, at least one of the one or more channels extending distally from the EUS instrument 100 may be an air and water channel (not shown). Additionally, or alternatively, a second channel extending distally from the EUS instrument 100 may be a suction channel (not shown).

In yet a further exemplary embodiment, the EUS instrument 100 may include circuitry (e.g., a circuit boards or the like) and/or one or more mechanisms (e.g., mechanical devices and/or assemblies) for controlling one or more operations of the EUS instrument 100 and/or EUS system. The circuitry may be included in the handheld portion 102 (e.g., in the casing 104) or operably connected to parts of the EUS instrument 100.

Additionally, or alternatively, the circuitry and/or mechanical devices may be provided at one or more of the EUS system operably connected to the EUS instrument 100, and controlled remotely therefrom via one or more assemblies operably connected to the handheld portion 102 (e.g., any valve assemblies) and/or the controllers 110.

With continued reference to the figures, and now with reference to FIG. 2A and FIG. 2B, at least one of the valve assemblies operably secured or otherwise removably attached to the EUS instrument 100, and more particularly, to at least one of the first cylinder 106 or second cylinder 108 may be an air and water (AW) valve assembly 200.

It should be appreciated that embodiments of the EUS instrument 100 having primarily the AW valve assembly 200 may be referred to herein as an AW supply apparatus or device.

In one exemplary embodiment, the AW valve assembly 200 may be a disposable AW valve assembly 200 (e.g., formed from disposable materials and/or constructed of materials having a reduced purchase and/or use costs than any traditional valves) and may include at least an AW valve part 210 at least partially disposed between an endcap 250, and in some embodiments, an AW endcap cover 294 adapted to cover at least a portion of the endcap 250 and the AW valve part 210 when fully assembled. The AW valve assembly 200 may further include a cap 270 (FIG. 2E) adapted to cover one or more parts of the AW valve assembly 200 when assembled, and when the cap 270 is secured (e.g., removably secured) to one end of the AW valve part 210.

In some embodiments, for example, as shown in FIG. 2C and FIG. 2D, the AW valve part 210 may include at least a first stem 212 and a second stem 214. The first stem 212 and the second stem 214 may be formed from different materials. However, it should be appreciated that similar materials may be used for forming both the first stem 212 and the second stem 214. In some embodiments, for example, the first stem 212 may be comprised of primarily metals or metallic-like materials, and the second stem 214 may be comprised of primarily polymers or polymer-like materials. The first stem 212 may be a single piece construction (i.e., a single piece) formed of a single continuous material molded and/or otherwise formed or fabricated into the embodiments of the first stem 212 described herein. Additionally, or alternatively, the second stem 214 may be a single piece construction (i.e., a single piece) formed of a single continuous material molded and/or otherwise formed or fabricated into embodiments of the embodiments of the second stem 214 described herein.

With continued reference to the figures, the first stem 212 may include a body 216 having a first end 218, which may be the proximal end, and a second end 220, which may be the distal end. The body 216 may be elongated and include a hollow portion defining a channel CH (FIG. 2D) extending between an opening 222 (e.g., a proximal orifice) at the first end 218 and towards the second end 220. In some embodiments, the channel CH may extend towards the second end 220 to a point where the body 216 transitions from the hollow portion to a threaded portion 224 at the second end 220. Additionally, or alternatively, the channel CH may extend from the opening 222 and beyond one or more apertures or similar openings 226 extending at least partially through a thickness of the body 216 until the channel CH concludes at the portion of the body 216 where the threaded portion 224 may begin.

One or more of the openings 226 extending through a thickness of the body 216 may be sized or otherwise shaped for controlling the passage of air and/or water into and out of the channel CH, for example, during an EUS procedure. With continued reference to FIG. 2D, the body 216 may include three openings 226 (also referred to as multiple openings) formed through the thickness of the body 216 and channel CH. As shown, the portion of the body 216 having the multiple openings 226 may having a larger diameter than the threaded portion 224 at the second end 220. Additionally, or alternatively, the portion of the body 216 having the multiple openings 226 may have a smaller diameter than a second threaded portion 228 at the first end 218 proximate to the opening 222.

In some embodiments, the body 216 may include a flange 230 extending around a perimeter of the body 216 at the first end 218. As illustrated in the figures, the flange 230 may be positioned or otherwise defined between the opening 222 at the first end 218 and the portion of the body 216 having the multiple openings 226 such that the flange 230 may separate portions of the body 216 having different diameters. For example, the flange 230 may separate the smaller diameter portion of the body with multiple openings 226 from the larger diameter portion of the body 216 where the opening 222 at the first end 218 is defined.

Additionally, or alternatively, the flange 230 may only extend outwardly from the body 216. That is, the flange 230 may not extend through the channel CH so as to obstruct (partially or fully) the channel CH so that air and/or fluids may flow unobstructed through the channel CH, the opening 222 at the first end 218, the area where the flange 230 is formed, and/or any of the multiple openings 226 as needed.

In some embodiments, the second threaded portion 228 formed on the larger diameter portion of the body 216 may extend from the opening 222 at the first end 218 or proximate thereto towards the flange 230 such that only a portion of the body 216 between the opening 222 at the first end 218 and the flange 230 may be threaded (i.e., may be the second threaded portion 228), while the remaining part may be unaltered (e.g., in a condition as fabricated and/or non-threaded). In some embodiments, the full area between the opening 222 at the first end 218 and the flange 230 may be threaded.

With continued reference to the figures, the first threaded portion 224 may differ from the second threaded portion 228 in that the first threaded portion 224 may be a trilobular (also referred to as tri-lobe) threaded portion and the second threaded portion 228 may be a machine threaded portion and/or a roll threaded portion. It should be appreciated that in lieu of a machine threaded and/or roll threaded portion, one or more of the parts may be frictionally fitted by mean known to persons of ordinary skill in the art.

In some embodiments, the second threaded portion 228 may be sized or otherwise adapted to securing the body 216 to the cap 270 at the first end 218. It should be appreciated that, in some embodiments, in lieu of or in addition to the second threaded portion 228, the cap 270 may be snapped or similarly frictionally secured to the body 216 at the first end 218 by other securing or attaching means known to persons of ordinary skill in the art. It should further be appreciated that for securing the cap 270 to the body 216 (e.g., via the second threaded portion 228), the cap 270 may include threading and/or a plurality of grooves 272 (FIG. 2B) that may correspond to a threading pattern of the second threaded portion 228 for rotatably securing the cap 270 to the body 216.

Figure 2F:
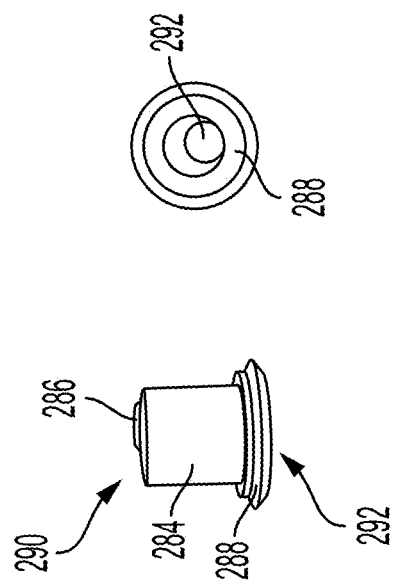
FIG. 2F illustrates a sideview and underside view of a spring guide in accordance with the disclosure provided herein.
Figure 2E:
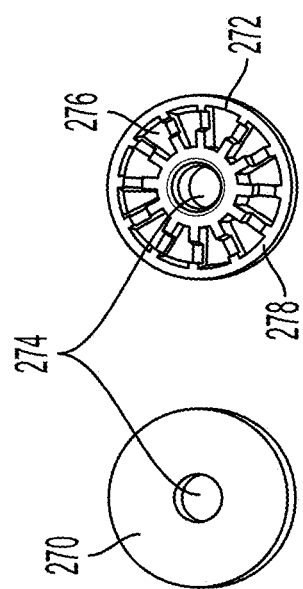
FIG. 2E illustrates a topside and underside view of a cap in accordance with the disclosure provided herein.

With continued reference to the figures, and with reference now to FIG. 2E, the cap 270 may further include an opening 274 extending through the cap 270, for example, from a topside of the cap 270 towards an underside of the cap 270. The opening 274 may be formed at or proximate to a center of the cap 270, and may be aligned with the opening 222 formed at the first end 218 of the body 216 when secured to the body 216. In some embodiments, the grooves 272 corresponding to the second threaded portion 228 may be formed within the opening 274. In one exemplary embodiment, the full opening 274 may include grooves 272 for securing the body 216 thereto, or in some embodiments, at least a portion of the opening 274 may include grooves 272 defined therein.

The opening 274 may be sized or otherwise adapted to receive at least a portion of the first end 218 of the body 216, which may include only the second threaded portion 228 and not the non-threaded portion of the first end 218 between the flange 230 and the area where the second threaded portion 228 begins. It should be appreciated that when secured to the cap 270, the first end 218 of the body 216 may extend up to the opening 274 or beyond the topside of the cap 270 based on where the second threaded portion 228 ends and the non-threaded portion begins on the first end 218.

In yet a further exemplary embodiment, at least a portion of the underside of the cap 270 may be recessed or otherwise adapted for interfacing with a first spring 280 of the AW valve assembly 200. This spring adapted area (also referred to as a recessed portion 276) on the underside of the cap 270 may define an area at the underside of the cap 270 for seating the first spring 280 when the AW valve assembly 200 is assembled. In some embodiments, the recessed portion 276 sits between a cap wall 278 formed around a perimeter of the cap 270. The cap wall 278 may be sized or otherwise shaped to restrict a lateral movement of the first spring 280, for example, when depressing the cap 270 such that the first spring 280 is compressed directionally towards the second end 220. In some embodiments, the cap wall 278 may extend downwardly from the topside of the cap 270 to a height that may be shorter (less) than or equal to a thickness of the cap 270 between the topside and the lowest part of the underside of the cap 270.

With continued reference to the figures, the second stem 214 may be a valve stem and includes a valve stem body 232 having a first end 234 and a second end 236. It should be appreciated that the geometry of the valve stem body 232 may correspond to an interior of one or more of the first cylinder 106 and/or second cylinder 108 such that the valve stem body 232 may sealingly engage the interior of the first cylinder 106 when the AW valve assembly 200 is inserted therein. In some embodiments, and for sealingly engaging the interior, the second stem 214 may include one or more seals 238 selectively attached to the valve stem body 232. The seals 238 may be secured (e.g., frictionally or by other means known to persons of ordinary skill in the art) to one or more cylinders or designated areas along the valve stem body 232. It should be appreciated that the seals 238 may be situated or otherwise positioned on the valve stem body 232 to sealingly engage the AW valve assembly 200 within the casing 104 in operation (e.g., during the EUS procedure).

In the embodiment illustrated in FIG. 2C, three seals 238 are shown attached to the valve stem body 232, with a first seal proximate to or at the first end 234, a second seal proximate to or at the second end 236, and a third seal attached proximate to a center of the valve stem body 232, and positioned between a shoulder 240 protruding from or otherwise formed in the valve stem body 232 and the second seal proximate to the second end 236.

In some embodiments, the valve stem body 232 may include an opening 242 at the first end 234 and be sealed or otherwise closed at the second end 236. The opening 242 at the first end 234 may be adapted or otherwise sized and/or shaped for receiving at least a portion of the first stem 212 (e.g., the threaded portion 224). It should be appreciated that the threaded portion 224 may be inserted into opening 242 at the first end 234 such that the portion of the body 216 with the multiple openings 226 abuts or interfaces with the valve stem body 232 at the first end 234 when the threaded portion 224 is fully disposed within the opening 242 at the first end 234 of the valve stem body 232. It should be appreciated that the valve stem body 232 may be hollow for receiving the threaded portion 224 therein.

The hollow portion of the valve stem body 232 may fully extend towards the second end 236, or in some embodiments, to a distance towards the second end 236 for fully encompassing the threaded portion 224. It should be appreciated that the hollow portion of the valve stem body 232 may include grooves corresponding to the threaded portion 224. It should further be appreciated that in an embodiment where the threaded portion 224 is a trilobular threaded portion (e.g., a portion having triangular thread forming threads), no grooves may be provided in the hollow portion.

The trilobular threading may be provided for its ability to reduce the stresses of threading into a plastic. In some embodiments, when securing the threaded portion 224 to the second stem 214, the hollow portion of the valve stem body 232 may be formed via the thread forming threading of the threaded portion 224. It should be appreciated that the second stem 214 may be formed from a polymer construction and forming the hollow portion via the trilobular threading may be achieved without compromising the integrity of the second stem 214.

With continued reference to the figures, and now with reference to FIG. 2G, the endcap 250 may include an endcap body 252 having a first end 254 and a second end 256, and a plurality of openings formed between the first end 254 and second end 256. In some embodiments, the endcap body 252 or portions thereof may be hollow for receiving one or more parts of the AW valve assembly 200 therein, for example, the first stem 212, the first spring 280, etc., via the first end 254.

In the exemplary embodiment of FIG. 2G, a first opening 258 may be provided at the first end 254 for receiving at least the first stem 212 therein. A second opening 260 which may be smaller than the first opening may be provided at the second end 256 to allow for portions of the first stem 212 (e.g., the threaded portion 224) to extend therethrough for securing the threaded portion 224 to the second stem 214 when the threaded portion 224 is extending through the second opening 260.

Additionally, or alternatively, a third opening (intermediate opening) 262 may be formed within the endcap 250 between the first opening 258 and second opening 260. In this exemplary embodiment, the intermediate opening 262 may be smaller than the first opening 258 and larger than the second opening 260.

As shown in FIG. 2G, the hollow portion of the endcap 250 extending between the first opening 258 and the intermediate opening 262 may be constant (i.e., having a same diameter) towards a first platform 264 formed in an interior of the endcap 250 and near or at a center of the endcap 250. It should be appreciated that the intermediate opening 262 may be formed in the first platform 264. In some embodiments, the size (e.g., the diameter) of the intermediate opening 262 may be greater or equal to the size of the flange 230 such that the flange 230 may be received between the intermediate opening 262.

With continued reference to the figures, a second platform 266 may be formed between the first platform 264 and the second end 256 of the endcap 250. The second opening 260 may be formed in the second platform 266, and may be sized to allow for passage of the threaded portion 224 therethrough and not the flange 230. It should be appreciated that in this embodiment, the flange 230 may engage the second platform 266 such that the second platform 266 restricts a movement of the first stem 212 beyond a point where the flange 230 engages the second platform 266.

In some embodiments, the flange 230 may sit below the first platform 264 when engaging the second platform 266 without a second spring 282 and/or spring guide 284 disposed between the flange 230 and the second platform 266. It should be appreciated that a distance between the first platform 264 and the second platform 266 may be based a height of the flange 230. It should further be appreciated that the second spring 282 may be sized such that it may be at least partially disposed between the intermediate opening 262 of the first platform 264 to engage or be compressed against the second platform 266.

In some embodiments, the second spring 282 and the first spring 280 may be differently sized and/or coiled. For example, the second spring 282 may be smaller than the first spring 280 and more tightly coiled. It should be appreciated that similarly sized and coiled springs may be also used, depending on the use and geometry of the valve embodiments described herein.

In some embodiments, the first platform 264 may include a plurality of openings extending downwardly towards the second end 256 and through a thickness of the first platform 264. One or more of the first platform 264 openings may be provided to allow for the passage of air therethrough.

Additionally, or alternatively, the second platform 266 may include a plurality of openings extending downwardly towards the second end 256. The openings in the second platform 266 may be sealed, for example, via one or more endcap seals 268 (at least three shown in FIG. 2H). One or more of the second platform 266 openings may be provided for a mechanical advantage (e.g., to mechanically hold the elastomer in place).

With reference now to FIG. 2F, the spring guide 284 may be hollow or define a hollow interior and may include a first opening 290 at the first end of the spring guide 284 and a second opening 292 at a second opposite end of the spring guide 284. In some embodiments, the second opening 292 at the second end of the spring guide 284 may be larger in diameter than the first opening 290 at the first end of the spring guide 284.

The spring guide 284 may be shaped or otherwise sized to allow for the first spring 280 to be installed over portions of the spring guide 284 such that the spring guide 284 may be at least partially disposed within the first spring 280. In some embodiments, a guide shoulder or similar flange may be provided at the second end of the spring guide 284 and may extend outwardly therefrom. The guide shoulder may function as a stop for the first spring 280 when the first spring 280 is installed over the spring guide 284. In this embodiment, the guide should may restrict or otherwise limit the first spring 280 from moving beyond the stop, and in some embodiments, the second end of the spring guide 284 when assembled. Additionally, or alternatively, the second opening 292 at the second end of the spring guide 284 and the hollow interior of the spring guide 284 may be shaped or otherwise sized for at least partially receiving the second spring 282 within the hollow interior.

With continued reference to the figures, the spring guide 284 may include a first guide seal 286 at a first end of the spring guide 284 and a second guide seal 288 at an opposite second end of the spring guide 284.

The first guide seal 286 may be positioned on one side (e.g. a topside) of the spring guide 284 (e.g., closest to the first end 254) and around a perimeter of the first opening 290 at the first end such that at least part of the topside of the spring guide 284 includes the first guide seal 286 for engaging the underside of the cap 270 when depressing the cap 270 in operation (e.g., to a first depressed position).

Additionally, or alternatively, the second guide seal 288 may fully seal an underside of the spring guide 284 (e.g., closest to the second end 256) where the spring guide 284 (or the second guide seal 288) may engage the first platform 264 when the AW valve assembly 200 is assembled or when the spring guide 284 is seated within the endcap 250.

In some embodiments, the second guide seal 288 may extend from the underside of the spring guide 284 and upwardly through the second opening 292 and hollow interior towards the first end of the spring guide 284 and first end 254 of the endcap 250. The second guide seal 288 may extend to just below the first opening 290 of the spring guide 284 such that an inner portion of the first opening 290 remains unsealed by any of the guide seals.

With continued reference to the figures, assembling the AW valve assembly 200 may be achieved in the manner described below or via another manner as desired by an assembler, and so long as the assembled AW valve assembly 200 maintains its functionality.

In one exemplary embodiment, assembling the AW valve assembly may be achieved by first assembling the first stem 212, the cap 270, the first spring 280, and the spring guide 284. In this embodiment, the first end of the spring guide 284 may be inserted through one end of the first spring 280 such that the first spring 280 engages the outwardly extending shoulder at the second end of the spring guide 284.

Thereafter, the first end 218 of first stem 212 may be inserted through both the second end of the spring guide 284 and the first spring 280 to engage or otherwise be secured to the cap 270. It should be appreciated that the first spring 280 may be compressed for securing the first end 218 to the cap 270, and more particularly, for securing the second threaded portion 228 of the first stem 212 to the opening 274 of the cap 270.

Upon assembling at least an upper portion of the AW valve assembly 200 (i.e., securing the cap 270 to the first stem 212 with the first spring 280 disposed between the cap 270 and the stop of the spring guide 284), the second spring 282 may be installed or otherwise inserted into the second end and hollow interior of the spring guide 284 such that the second spring 282 covers portions of the second end 220 and the portion of the body 216 having the multiple openings 226. Thereafter, the second end 220 and second spring 282 may be inserted into the endcap 250 (e.g., via the first end 254) such that the second spring 282 may engage the second platform 266 and an underside of the spring guide 284 (or more particularly the second guide seal 288) may engage the first platform 264 within the endcap 250.

The second end 220 and second spring 282 should be inserted into the endcap 250 until the threaded portion 224 (or at least a part of the threaded portion 224) is exposed enough to begin securing (e.g., rotatably or frictionally securing) the second stem 214 to the first stem 212 via the threaded portion 224.

It should be appreciated that the second stem 214 should be secured to the first stem 212 via the threaded portion 224 until the second stem 214 is proximate to or abuts the second end 256 of the endcap 250.

Once the AW valve assembly 200 is assembled, the cap 270 may be depressed to a first position (e.g., a first tactile stop) and a second position (e.g. a second tactile stop). It should be appreciated that depressing the cap 270 to the first position may compress only the first spring 280 or second spring 282, while depressing the cap 270 to the second position may compress both the first spring 280 and the second spring 282.

With continued reference to the figures, and now with reference to FIG. 3A, FIG. 3B, and FIG. 3C, at least one of the valve assemblies for operably securing or otherwise removably attaching to the EUS instrument 100, and more particularly, to at least one of the first cylinder 106 or second cylinder 108 may be a suction valve (SV) assembly 300. It should be appreciated that embodiments of the EUS instrument 100 having primarily the suction valve assembly 300 may be referred to herein as a suction supply apparatus or device.

It should further be appreciated that the AW valve assembly 200 and the suction valve assembly 300 may be provided to control the air and water function and the suction function on an EUS instrument 100, as well as an inflation and deflation of an EUS balloon during the EUS procedure (e.g., a GI ultrasonic endoscopic procedure). The AW valve assembly 200 may further be provided to assist with cleaning an objective lens during the EUS procedure.

The suction valve assembly 300 may be a disposable (e.g., formed from disposable materials and/or constructed of materials having a reduced purchase and/or use costs than traditional valves).

In some embodiments, the suction valve assembly 300 may include at least an SV endcap 302 configured to at least partially receive one or more parts of the suction valve assembly 300. The suction valve assembly 300 may further include an SV endcap cover 304 (FIG. 3A) adapted to cover at least a portion of the SV endcap 302. In some embodiments, the SV endcap cover 304 (or AW endcap cover 294) may be substantially cylindrical and/or have a cylindrical shape for being inserted in the casing 104, or more particularly, the first cylinder 106 and/or second cylinder 108. It should be appreciated that additional shapes (e.g., polygonal shapes) may be utilized for the SV endcap cover 304 and/or the AW endcap cover 294. In these embodiments, for example, the polygonal shaped endcaps may correspond to a similarly shaped opening of the casing 104 for at least partially receiving the valve assemblies.

Figure 3D:
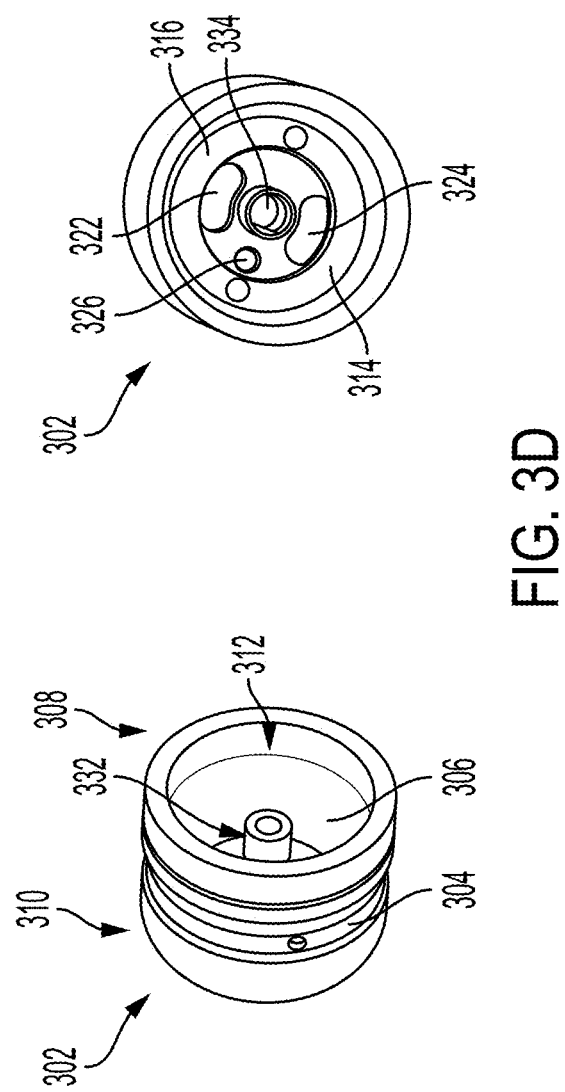
FIG. 3D illustrates an exemplary embodiment of an SV endcap in accordance with the disclosure provided herein.
Figure 3E:
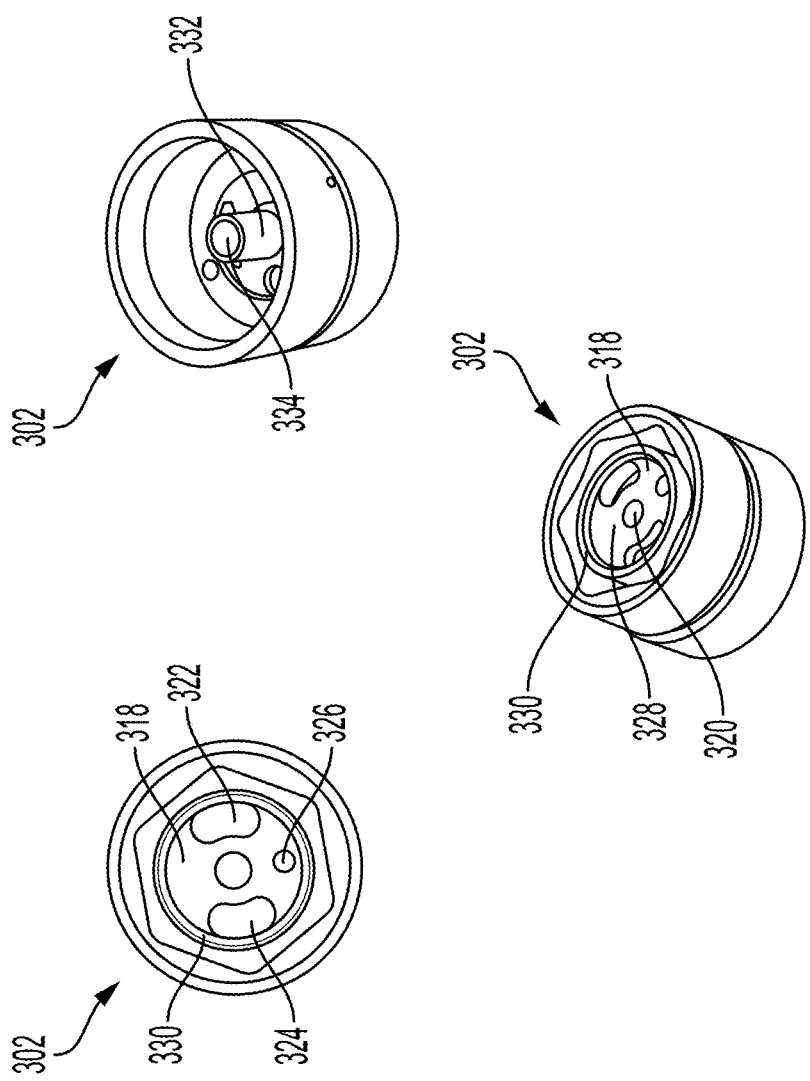
FIG. 3E illustrates perspective views of embodiments of the SV endcap of FIG. 3A.

With continued reference to the figures, and now with reference to FIGS. 3D and 3E, the SV endcap 302 includes at least an SV endcap body 306 having a first end 308 and a second end 310, and a plurality of openings formed between the first end 308 and second end 310.

In some embodiments, the SV endcap body 306 may be hollow. Additionally, or alternatively, the SV endcap body 306 may be generally cylindrical (e.g., forming a tube). As shown in FIG. 3D, the SV endcap body 306 may include a first opening 312 at the first end 308 leading into the hollow area. The hollow area may extend from the first end 308 towards an SV endcap wall 314 defined or otherwise positioned at or proximate to the second end 310 of the SV endcap body 306. The hollow area defined within the SV endcap body 306 may be sized or otherwise shaped to at least partially receive one or more parts of the suction valve assembly 300 therein (e.g., a piston, one or more springs etc.) when the suction valve assembly 300 is assembled (partially and/or fully). In some embodiments, the SV endcap wall 314 may be provided to restrict or limit a movement of one or more parts at least partially received within the hollow area of the SV endcap body 306.

The SV endcap wall 314 may include an inner surface 316, which may be the side of the SV endcap wall 314 within the hollow area facing the first end 308. The SV endcap wall may further include an outer surface 318 (FIG. 3E) facing in the opposite direction from the inner surface 316.

With continued reference to the figures, the SV endcap wall 314 may include one or more openings extending through a thickness of the SV endcap wall 314. In one exemplary embodiment, the SV endcap wall 314 may include a first wall opening 320 extending through a thickness of the SV endcap wall 314. In some embodiments, the first wall opening 320 may be sized or otherwise shaped for receiving at least a portion of one or more SV stems therebetween. As shown in FIG. 3E, the first wall opening 320 may be included at or proximate to a center of the SV endcap wall 314.

Additionally, or alternatively, the SV endcap wall 314 may include at least a second wall opening 322 extending through a thickness of the SV endcap wall 314. The second wall opening 322 may be sized or otherwise shaped to allow portions of a piston and/or one or more SV stems to be at least partially extended therethrough for operably connecting the piston to at least one of the SV stems at least via the second wall opening 322. In some embodiments, as illustrated in FIG. 3E, a third wall opening 324 may also be provided for operably connecting the piston to the SV stem. As shown, the third wall opening 324 may be similar in size and shape to the second wall opening 322.

In yet a further exemplary embodiment, the SV endcap wall 314 may include a fourth wall opening 326 extending through a thickness of the SV endcap wall 314. In some embodiments, the fourth wall opening 326 may be sized or otherwise shaped for receiving at least a portion of one or more SV stems therethrough. Additionally, or alternatively, the fourth wall opening 326 may be sized or otherwise shaped to clock position the guide pin 354 in relation to a stem (e.g., the second SV stem 360), which may be formed of metals.

With continued reference to FIG. 3E, a least a portion of the outer surface 318 of the SV endcap wall 314 may be recessed such that the SV endcap wall 314 is offset from the outermost edge of the SV endcap body 306 at the second end 310. The recessed portion 328 may define a lip 330 extending around a perimeter of the SV endcap body 306 at the second end 310. It should be appreciated that a surface area of the recessed portion 328 may be less than a surface area of a non-recessed outer surface 318.

In some embodiments, the diameter of recessed portion 328 may be less than a diameter of the SV endcap body 306 at the second end 310. Additionally, or alternatively, the recessed portion 328 diameter may be equal to or greater than a diameter of the stem body 342 (FIG. 3F) to allow for the stem body 342 to sit (e.g., flush) within the recessed portion 328 such that the lip 330 may assist to restrict or otherwise limit a movement (e.g., a lateral movement) of the of the first SV stem 340 when seated.

In some embodiments, the height of the lip 330, which may be measured from the outer surface 318 of the recessed portion 328 to the distal most point of the lip 330 may be equal to a thickness T (FIG. 3F) of the stem body 342 such that the stem body 342 may be flush with the lip 330 at the second end 310.

In yet a further exemplary embodiment, a guide member 332 may be provided in the hollow area of the SV endcap 302. In some embodiments, the guide member 332 may be formed from the inner surface 316 of the SV endcap wall 314 such that the guide member 332 is integral with the SV endcap wall 314. Additionally, or alternatively, the guide member 332 may be selectively attached to the inner surface 316 via an adhesive, fastener, or similar securing mechanism known in the art and capable of securing the guide member 332 to the inner surface 316.

In some embodiments, the guide member 332 may include a guide opening 334 sized or otherwise shaped to allow at least a portion of an SV stem (e.g., a second SV stem 360 (FIG. 3H)) to pass therebetween when assembling the suction valve assembly 300.

The guide member 332 may be positioned at or proximate to the center of the SV endcap wall 314 such that the first wall opening 320 may be aligned (substantially or fully aligned) with the guide opening 334 to allow passage of the second SV stem 360 at least partially through both the first wall opening 320 and the guide opening 334.

In some embodiments, the guide member 332 may be cylindrical (e.g., tubular shaped) and may extend from the inner surface 316 towards the first end 308. In this embodiment, the guide member 332 may extend in a proximal direction towards the first end 308 such that a tip of the guide member 332 may be proximate to or beyond a midpoint of the hollow area within the SV endcap body 306. It should be appreciated that the guide opening 334 may extend fully through the guide member 332. In some embodiments, the guide opening 334 may be generally circular.

Additionally, or alternatively, at least a portion of the guide opening 334 may be flat or otherwise shaped to correspond with similarly shaped portions of the second SV stem 360.

Figure 3F:
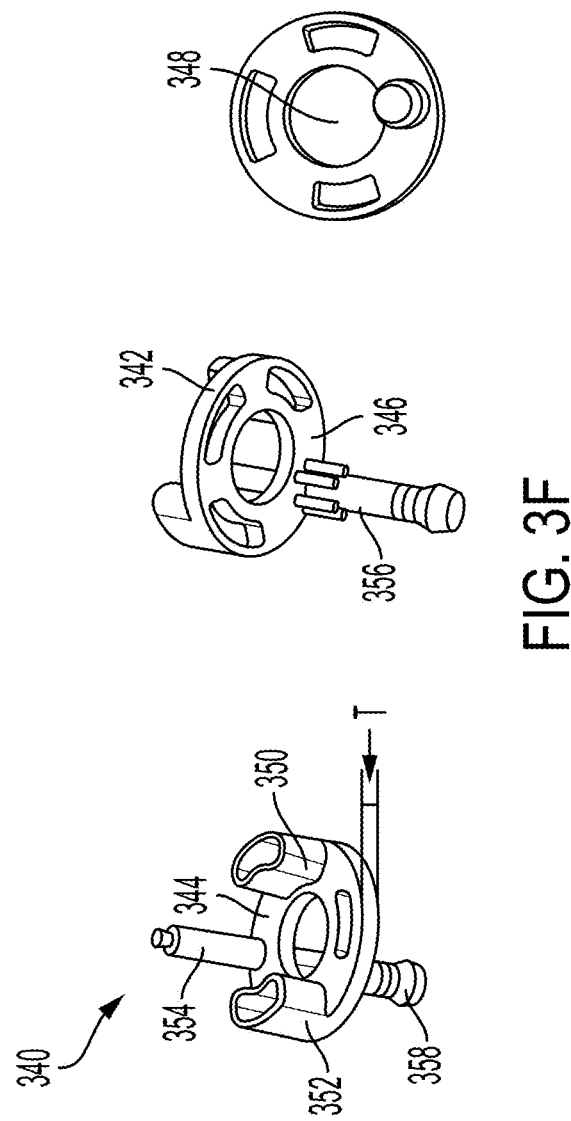
FIG. 3F illustrates an exemplary embodiment of a first SV stem in accordance with the disclosure provided herein.
Figure 3G:
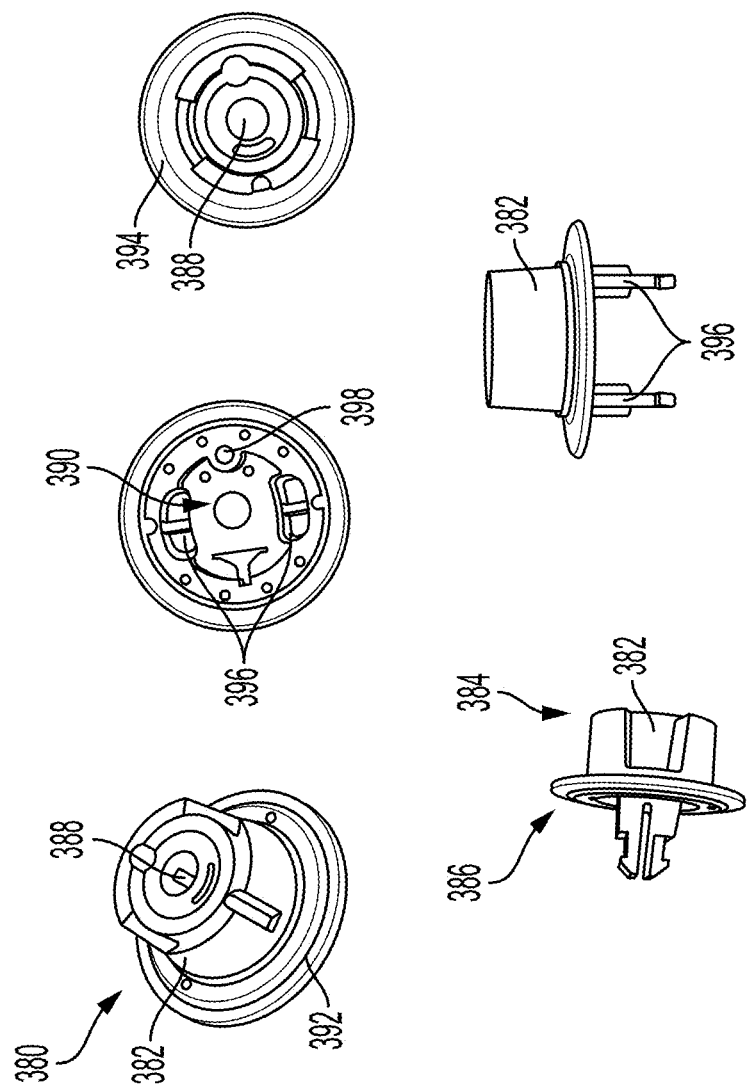
FIG. 3G illustrates an exemplary embodiment of a piston (e.g., a spring guide piston) in accordance with the disclosure provided herein.
Figure 3I:
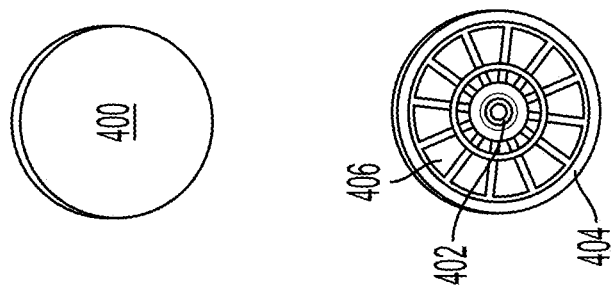
FIG. 3I illustrates an exemplary embodiment of an SV cap in accordance with the disclosure provided herein.
Figure 3H:
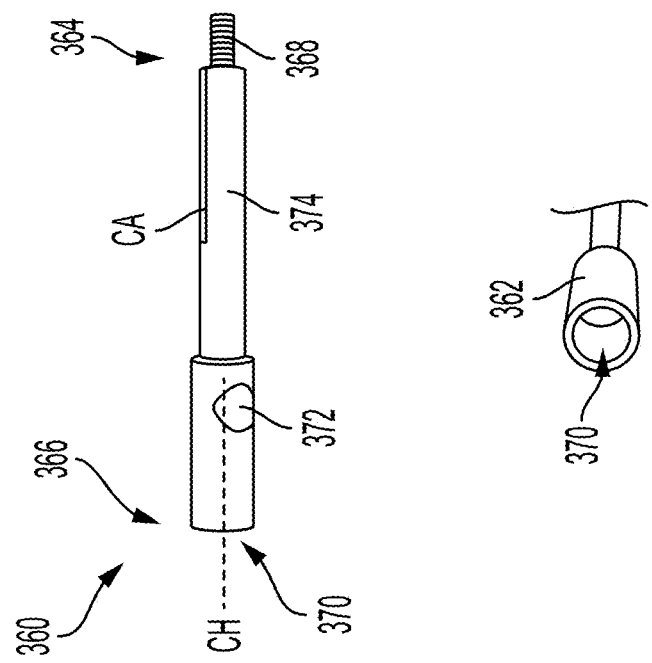
FIG. 3H illustrates an exemplary embodiment of a second SV stem in accordance with the disclosure provided herein.

For example, as shown in FIG. 3H, the guide opening 334 includes a flat portion that correspond with a flat portion of the second SV stem 360.

It should be appreciated that the flat portion may assist to ensure proper fitment and/or alignment of the SV stem (e.g., the second SV stem 360) through the guide member 332, and more particularly the guide opening 334. It should further be appreciated that the flat portion may be provided to restrict or otherwise limit a movement of the second SV stem 360 when inserted through the first wall opening 320 (which may be generally circular) and the guide opening 334 (which may include both circular and flat portions).

Additionally, or alternatively, the guide member 332 may be provided as a place holder or similar guide for one or more springs of the suction valve assembly 300 (e.g., the second spring 378). It should be appreciated that the guide member 332 may be sized or shaped such that the second spring 378 may sit over at least a portion of the guide member 332 when assembled. In some embodiments, the guide member 332 may extend to a midpoint of the second spring 378 when the second spring 378 is installed over the guide member 332.

With continue reference to the figures, and now with reference to FIG. 3F, the suction valve assembly 300 may include at least a first SV stem 340 and a second SV stem 360. In some embodiments, the first SV stem 340 and the second SV stem 360 may be formed from different materials. However, it should be appreciated that similar materials may be used for forming both the first SV stem 340 and the second SV stem 360. In some embodiments, for example, the first SV stem 340 may be comprised of primarily polymers or polymer-like materials, and the second SV stem 360 may be comprised of primarily metals or metallic-like materials. The first SV stem 340 may be a single piece construction (i.e., a single piece) formed of a single continuous material molded and/or otherwise formed or fabricated into the embodiments of the first SV stem 340 described herein. Additionally, or alternatively, the second SV stem 360 may be a single piece construction (i.e., a single piece) formed of a single continuous material molded and/or otherwise formed or fabricated into embodiments of the embodiments of the second SV stem 360 described herein. Additionally, or alternatively, each of the first SV stem 340 and the second SV stem 360 may be a single piece construction formed from multiple materials molded and/or otherwise formed or fabricated into the embodiments described herein.

As illustrated in the embodiment of FIG. 3F, the first SV stem 340 may include a stem body 342 having a first side 344 and a second side 346 opposite the first side 344. The stem body 342 may include one or more openings extending through a thickness T of the stem body 342.

In some embodiments, the stem body 342 may include a first opening 348 extending through a thickness T of the stem body 342. The first opening 348 may be sized or otherwise shaped for receiving at least a portion of the second SV stem 360 therethrough when the suction valve assembly 300 is assembled.

The stem body 342 may further include one or more ports (e.g., connection ports) extending from the first side 344 (e.g., in a proximal direction) for connecting the first SV stem 340 to one or more other parts of the suction valve assembly 300 (e.g., the piston 380). In the embodiment of FIG. 3F, for example, a first connecting port 350 and a second connecting port 352 are provided. Each of the first connecting port 350 and the second connecting port 352 may include an opening for receiving at least a portion of a connecting means (e.g., piston clips 396) of the piston 380 to connect the first SV stem 340 to the piston 380 via corresponding openings in the SV endcap wall 314. The first connecting port 350 and the second connecting port 352 may be sized or otherwise shaped for being at least partially disposed or otherwise inserted via the second wall opening 322 and/or the third wall opening 324 for connecting to the piston clips 396.

In some embodiments, the first SV stem 340 may include a guide pin 354. The guide pin 354 may be provided to guide and/or position the first SV stem 340 during assembly, and to ensure proper fitting and/or alignment of the first SV stem 340 with, for example, the piston 380. The guide pin 354 may further be provided to maintain the clocking relationship between the first SV stem 340, the piston 380, and/or the SV endcap 302. The guide pin 354 may be sized or otherwise shaped for being installed or otherwise inserted via the fourth wall opening 326 of the SV endcap wall 314 and to interface or otherwise engage an opening (e.g., a guide opening 398 (FIG. 3G)) of the piston 380.

With continue reference to the figures, the stem body 342 may further include one or more sleeves 356 extending from the second side 346 of the stem body 342. In one embodiment, the sleeve 356 may be an orientation clocking sleeve.

The orientation clocking sleeve may be provided for guiding an assembled suction valve assembly 300 to the insertion location of the second cylinder 108. In some embodiments, the orientation clocking sleeve may include one or more ribs extending therefrom to facilitate aligning the orientation clocking sleeve within the second cylinder 108. It should be appreciated that the ribs may have any size and/or shape based on a shape and/or size of the corresponding insertion location of the second cylinder 108. In some embodiments, a stem seal 358 (e.g., a balloon suction seal) may be provided at a distal end of the sleeve 356.

With continued reference to the figures, and now with reference to FIG. 3H, the second SV stem 360 may be a valve stem and may include a valve stem body 362 having a first end 364, which may be the proximal end, and a second end 366, which may be the distal end. As illustrated in FIG. 3H, the valve stem body 362 may include a threaded portion provided or otherwise formed at the first end 364, and a first opening 370 provided or otherwise formed at the second end 366.

In some embodiments, the threaded portion may be a stem threaded portion 368. The stem threaded portion 368 may be provided for securing the second SV stem 360 to an SV cap 400. The first opening 370 may be generally circular and may have a larger diameter than a diameter of the stem threaded portion 368.

In some embodiments, the valve stem body 362 may be elongated and may include a hollow portion defining a channel CH at the second end 366. The channel CH may extend in a proximal direction from the first end 364 and concluding where the solid portion 374 begins. In some embodiments, the diameter or size of the solid portion 374 may be less than the diameter of the first opening 370 and greater than the diameter of the stem threaded portion 368.

With continued reference to the figures, a second opening 372 into the channel CH may be provided at or proximate to the first end 364. The second opening 372 may extend only through one side of the valve stem body 362. Described another way, the second opening 372 may not extend completely through the valve stem body 362, but instead, merely provides a side opening into the channel CH. In some embodiments, the channel CH may extend in a proximal direction towards the first end 364 concluding just beyond the second opening 372 in the side wall. In some embodiments, and depending on the position in the second cylinder 108, the second opening 372 may provide a suction (or non-suction) path from the distal end of the endoscope.

Additionally, or alternatively, at least a portion of the valve stem body 362 may not be hollow (e.g., between the hollow portion and the stem threaded portion 368), and instead, may be a solid portion 374. Additionally, or alternatively, at least a portion of the valve stem body 362 (e.g., the solid portion 374) may include a clocking/orientation area CA. The clocking/orientation area CA may orient the position of the valve stem body 362 for aligning the second opening 372, for example, in the second cylinder 108.

Figure 3J:
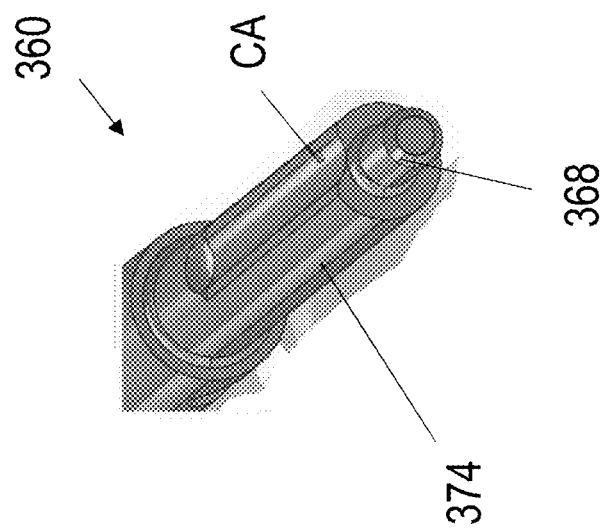
FIG. 3J illustrates a perspective view of an exemplary embodiment of a valve stem body in accordance with the disclosure provided herein.

In some embodiments, a profile or shape of the clocking/orientation area CA may correspond to one or more openings of the suction valve assembly 300 (e.g., the first wall opening 320 and/or the guide opening 334). For example, a flat clocking/orientation area CA may correspond to an opening in the suction valve assembly 300 with flat portions, or in some embodiments, as illustrated in FIG. 3J, the clocking/orientation area CA may have an arcuate profile (e.g., include a curved portion) which may correspond to an opening in the suction valve assembly 300 with curved portions. It should be appreciated that other profiles and/or shapes for the clocking/orientation area CA may be provided, and which may be based on a corresponding opening in the suction valve assembly 300.

With continue reference to the figures, and now with reference to FIG. 3G, the suction valve assembly 300 may include a piston 380. The piston 380 may be sized and shaped or otherwise adapted to interface and/or connect to a first SV stem 340 via at least the SV endcap 302 when assembled (e.g., fully assembled). In some embodiments, the piston 380 may be a single piece construction (i.e., a single piece) formed of a single continuous material molded and/or otherwise formed or fabricated into the embodiments of the piston 380 described herein. Additionally, or alternatively, the piston 380 may be formed by a combination of materials, which may include polymer and/or polymer-like materials, and/or elastomer and/or elastomer-like materials.

As illustrated in FIG. 3G, the piston 380 may include a piston body 382 having a first piston end 384 and a second piston end 386. The piston body 382 may be hollow and may include a first opening 388 at the first piston end 384 for receiving at least a portion of the second SV stem 360 therebetween when assembling the suction valve assembly 300 and securing the second SV stem 360 to the SV cap 400. Additionally, or alternatively, the piston body 382 may include a second opening 390 at the second piston end 386. The second opening 390 may lead into the hollow portion of the piston 380 and may be sized or otherwise adapted to cover at least a portion of a spring (e.g., the second spring 378) when assembled. In some embodiments, a diameter or the second opening 390 may be greater than a diameter of the first opening 388.

Additionally, or alternatively, the piston 380 may further include a piston flange 392 or similar platform formed at the second piston end 386 and extending outwardly from the piston body 382. In the embodiment of FIG. 3G, the piston flange 392 may extend around a perimeter of the piston body 382, and may at least be provided for supporting a first spring 376 disposed between the piston 380 and SV cap 400, when the first spring 376 is installed over the piston 380 during assembly of the suction valve assembly 300. It should be appreciated that, in some embodiments, the first spring 376 may be larger than the second spring 378. Additionally, or alternatively, the smaller second spring 378 may be wound tighter (i.e., coiled more tightly) than the larger first spring 376.

In some embodiments, the piston flange 392 may include a piston seal 394 selectively secure thereto. The piston seal 394 may be secured to at least an underside of the piston flange 392, or in a further exemplary embodiment, the piston seal 394 may fully cover the piston flange 392.

The piston 380 may further include one or more connecting means at the second piston end 386. The connecting means may extend in a distal direction from the piston body 382 and/or the piston flange 392 for connecting the piston 380 to at least the first SV stem 340.

In one embodiment, the connecting means may be one or more piston clips 396. In the embodiment of FIG. 3G a pair of piston clips 396 are provided on opposite sides of the second opening 390. The piston clips 396 may be sized or otherwise shaped for extending through at least the second wall opening 322 and the third wall opening 324, and/or for securing the piston 380 to the first SV stem 340.

In yet a further exemplary embodiment, the piston 380 may further include a third opening, which may be a guide opening 398. The guide opening 398 may be sized or otherwise adapted for receiving at least a portion of the guide pin 354 therebetween.

The suction valve assembly 300 may further include an SV cap 400 (FIG. 3I) adapted to cover one or more parts of the suction valve assembly 300 when assembled, and when the SV cap 400 is secured (e.g., removably secured) to an end of a threaded portion of an SV stem (e.g., the second SV stem 360). In some embodiments, the stem threaded portion 368 may be sized or otherwise adapted to securing the valve stem body 362 to the SV cap 400.

It should be appreciated that, in some embodiments, in lieu of or in addition to the stem threaded portion 368, the SV cap 400 may be snapped or similarly frictionally secured to the valve stem body 362 at the first end 364 by other securing or attaching means known to persons of ordinary skill in the art. It should further be appreciated that for securing the SV cap 400 to the valve stem body 362 (e.g., via the stem threaded portion 368), the SV cap 400 may include one or more cap inserts 402 (FIG. 3I) that may have a threading pattern or grooves that correspond to a threading pattern of the stem threaded portion 368 for rotatably securing the SV cap 400 to the valve stem body 362 during assembly.

Additionally, or alternatively, an underside of the SV cap 400 may include a void or similar recessed area extending at least partially through the SV cap 400, for example, from an underside of the SV cap 400. The void may be sized or otherwise shaped for being threaded (grooved) and/or for receiving a threaded part therein for securing the SV cap 400 to the stem threaded portion 368. The void may be formed at or proximate to a center of the SV cap 400. In some embodiments, the void with grooves and/or a threaded opening in the threaded part may be aligned with the stem threaded portion 368 when assembled for rotatably securing the SV cap 400 to the stem threaded portion 368.

With continued reference to the figures, and with reference now to FIG. 3I, at least a portion of the underside of the SV cap 400 may be configured or otherwise adapted for interfacing or otherwise engaging with a spring (e.g., a first spring 376) of the suction valve assembly 300 such that the first spring 376 sits within a recessed portion 406 of the SV cap 400 when the suction valve assembly 300 is assembled.

In some embodiments, an SV cap wall 404 may defined at on underside of the SV cap 400. The SV cap wall 404 may extend around a perimeter of the SV cap 400. The SV cap wall 404 may be sized or otherwise shaped to restrict or otherwise limit a lateral movement of a spring (e.g., the first spring 376), for example, during an EUS procedure. In some embodiments, a height of the SV cap wall 404 may be shorter than or equal to a thickness of the SV cap 400 to assist with limiting a lateral movement of the first spring 376. In some embodiments, the SV cap wall 404 (or AW cap wall) may define the area where the spring (e.g., the first spring 376) may sit when the valve assembly is assembled.

It should be appreciated that in operation, the EUS instrument 100 with the suction valve assembly 300 may be operably connected to a suction cylinder. Depressing the suction valve assembly 300, for example, to a first position (tactile stop) may cause a suction through an accessory channel (e.g., a suction channel) of or operably connected to the EUS instrument 100. Additionally, or alternatively, depressing the suction valve assembly 300, for example, to a second position (tactile stop) may cause water to be removed from an EUS balloon (e.g., during an EUS procedure).

In some embodiments, and during the EUS procedure, the EUS instrument 100 with the AW valve assembly 200 may be connected to an air and water cylinder. When connected to the air and water cylinder, air may flow through the opening 222 at the first end 218 (e.g., the proximal orifice). Adjusting and/or redirecting the air flowing through the AW valve assembly 200 via a zero position, which may include covering the proximal orifice, may cause air to flow through a lens cleaning channel of or operably connected to the EUS instrument 100. Depressing the AW valve assembly 200 to a first position (e.g., a first tactile stop) may force water through the lens cleaning channel resulting in water being deposited or otherwise placed on any objective lens, while depressing the AW valve assembly 200 to a second position (e.g., a second tactile stop) may feed water into the EUS balloon.

It is to be understood that the detailed description is intended to be illustrative, and not limiting to the embodiments described. Other embodiments will be apparent to those of skill in the art upon reading and understanding the above description. Moreover, in some instances, elements described with one embodiment may be readily adapted for use with other embodiments. Therefore, the methods and systems described herein are not limited to the specific details, the representative embodiments, or the illustrative examples shown and described. Accordingly, departures may be made from such details without departing from the spirit or scope of the general aspects of the present disclosure.

Additionally, the components and materials described hereinafter as making up the various embodiments are intended to be illustrative and not restrictive. It should be appreciated that many suitable components and materials that would perform the same or a similar function as the materials described herein are intended to be embraced within the scope of embodiments of the present disclosure.

We claim:

1. An endoscopy valve assembly comprising:
   an air and water (AW) valve; and
   an endcap configured to receive at least a portion of the AW valve therebetween;
   wherein the AW valve includes:
      a valve stem; and
      an AW stem having a channel extending distally from an opening in a proximal end of the AW stem, a proximal portion including a plurality of openings, and a distal end operable to be at least partially disposed within a valve stem opening at a proximal end of the valve stem to assemble the AW valve;
   wherein the AW stem and the valve stem are each formed of a single piece construction;
   wherein the channel of the AW stem terminates proximally to the valve stem when the AW valve is assembled; and
   wherein the proximal portion of the AW stem abuts the valve stem when the distal end is disposed within the valve stem.

2. The assembly of claim 1, wherein the AW stem is threaded at the distal end and at a proximal end.

3. The assembly of claim 2, wherein a first threading at the distal end of the AW stem is a tri-lobe threading adapted for being at least partially disposed within the valve stem opening.

4. The assembly of claim 3, wherein the tri-lobe threading is fully disposed within the valve stem opening.

5. The assembly of claim 3, wherein the valve stem opening includes grooves or threading corresponding to the tri-lobe threading at the one end of the AW stem but not the threading at the opposite end of the AW stem.

6. The assembly of claim 1, wherein the valve stem includes one or more seal slots.

7. The assembly of claim 6, further comprising;
   one or more valve seals positioned on one or more of the seal slots.

8. The assembly of claim 1, further comprising:
   a cap configured to cover at least a portion of the AW stem at an opposite end from the valve stem.

9. The assembly of claim 8, further comprising:
   a biasing member at least partially disposed within the endcap such that portions of the biasing member encloses parts of the AW stem between the cap and the endcap.

10. The assembly of claim 9, wherein the biasing member includes a spring and a spring guide configured to engage portions of the spring.

11. The assembly of claim 10, wherein the spring guide is positioned within the assembly to guide the spring along portions of the AW stem in operation.

12. The assembly of claim 1, wherein the AW stem includes an elongated AW stem body having a plurality of openings.

13. The assembly of claim 12, wherein the endcap comprises a plurality of openings and the AW stem extends through one or more of the plurality of openings of the endcap.

14. The assembly of claim 13, wherein the endcap further comprises a platform and the AW stem includes a flange, and wherein the flange of the AW stem operatively abuts the platform of the endcap to restrict movement of the AW stem through the endcap.

15. An endoscopic ultrasounds (EUS) instrument comprising:
   a casing having one or more casing openings configured to at least partially receive one or more valves assemblies therein; and
   an AW valve assembly according to claim 1 at least partially disposed in a first casing opening.

* * * * *